US009446238B2

(12) United States Patent
Lozano

(10) Patent No.: US 9,446,238 B2
(45) Date of Patent: Sep. 20, 2016

(54) DEEP BRAIN STIMULATION OF THE SUBCALLOSAL CINGULATE AREA FOR TREATMENT OF REFRACTORY ANOREXIA NERVOSA

(71) Applicant: Andres M. Lozano, Toronto (CA)

(72) Inventor: Andres M. Lozano, Toronto (CA)

( * ) Notice: Subject to any disclaimer, the term of this patent is extended or adjusted under 35 U.S.C. 154(b) by 115 days.

(21) Appl. No.: 14/163,979

(22) Filed: Jan. 24, 2014

(65) Prior Publication Data

US 2014/0357932 A1 Dec. 4, 2014

Related U.S. Application Data

(60) Provisional application No. 61/756,828, filed on Jan. 25, 2013.

(51) Int. Cl.
```
A61N 1/36      (2006.01)
A61N 2/00      (2006.01)
A61M 5/00      (2006.01)
A61N 1/05      (2006.01)
```

(52) U.S. Cl.
CPC ......... *A61N 1/3606* (2013.01); *A61N 1/36085* (2013.01); *A61N 1/0534* (2013.01); *A61N 1/36153* (2013.01); *A61N 1/36171* (2013.01); *A61N 1/36175* (2013.01); *A61N 2/006* (2013.01); *A61N 2001/36039* (2013.01)

(58) Field of Classification Search
CPC ........... A61N 1/0534; A61N 1/36085; A61N 1/36153; A61N 2001/36039; A61N 1/36175; A61N 1/3606; A61N 2/006; A61N 1/36171
See application file for complete search history.

(56) References Cited

U.S. PATENT DOCUMENTS

| | | | |
|---|---|---|---|
| 7,774,068 B1 | 8/2010 | Lozano | |
| 8,412,337 B2 | 4/2013 | Lozano | |
| 8,849,392 B2 | 9/2014 | Lozano | |
| 8,909,342 B2 | 12/2014 | Lozano | |
| 9,026,218 B2 | 5/2015 | Lozano et al. | |
| 9,227,066 B2 | 1/2016 | Lozano | |
| 2006/0212091 A1* | 9/2006 | Lozano | A61M 5/14276 607/45 |
| 2007/0027498 A1* | 2/2007 | Maschino | A61N 1/36082 607/45 |
| 2007/0100392 A1* | 5/2007 | Maschino | A61M 5/14276 607/45 |
| 2010/0057159 A1* | 3/2010 | Lozano | A61N 1/36096 607/45 |
| 2013/0231709 A1 | 9/2013 | Lozano | |
| 2013/0289385 A1 | 10/2013 | Lozano et al. | |
| 2014/0180194 A1 | 6/2014 | Lozano | |
| 2015/0142089 A1 | 5/2015 | Lozano et al. | |
| 2016/0030666 A1 | 2/2016 | Lozano et al. | |

OTHER PUBLICATIONS

Berkman ND, Bulik CM, Brownley KA, Lohr KN, Sedway JA, Rooks A, Gartlehner G (2006). "Management of eating disorders". Evid Rep Technol Assess (Full Rep) (135): 1-166.*
Bastiani AM, Altemus M, Pigott TA, Rubenstein C, Weltzin TE, Kaye WH. "Comparison of Obsessions and Compulsions in Patients with Anorexia Nervosa and Obsessive Compulsive Disorder". Biol Psychiatry 1996; 39:966--969.*

* cited by examiner

*Primary Examiner* — Christine H Matthews
*Assistant Examiner* — Joshua D Lannu

(57) ABSTRACT

In one embodiment, a method of treating an eating disorder in a patient, comprises: diagnosing the eating disorder in the patient; and electrically stimulating a subgenual cingulate cortex site or a ventral medial prefrontal cortex site in the patient using electrodes of an implanted stimulation lead.

7 Claims, 9 Drawing Sheets

A

B

DEEP BRAIN STIMULATION OF THE SUBCALLOSAL CINGULATE AREA FOR TREATMENT OF REFRACTORY ANOREXIA NERVOSA

CROSS-REFERENCE TO RELATED APPLICATION

This application claims priority to U.S. Provisional Patent Application Ser. No. 61/756,828, entitled "Deep Brain Stimulation of the Subcallosal Cingulate Area for Treatment of Refractory Anorexia Nervosa," filed Jan. 25, 2013, which is incorporated herein by reference in its entirety.

TECHNICAL FIELD

This application relates to stimulation of the subcallosal cingulate area for treatment of refractory anorexia nervosa and other eating disorders.

BACKGROUND

Some people suffer from chronic eating disorders, including anorexia and morbid obesity. The neural circuitry of the brain that controls eating and satiety include neurons in the lateral hypothalamus (feeding) and the ventral medial hypothalamus (satiety). U.S. Pat. Nos. 5,188,104 and 5,263,480 describe the use of electrical stimulation for treating eating disorders where the electrical stimulation was applied to the vagus nerve or to the trigeminal and/or glossopharyngeal nerve.

U.S. Pat. No. 5,782,798 describes a method for treating an eating disorder in a patient by stimulating and providing a drug to the central nervous system, in particular the paraventricular nucleus, lateral hypothalamus or ventral medial hypothalamus.

U.S. Pat. No. 6,950,707 describes a method for preventing an eating disorder in a patient by applying stimulus to the nucleus of the solitary tract.

While the aforementioned can provide some treatment and/or prevention of an eating disorder, the methods are not effective in the long term because they do not address many of the underlying behavioral factors and their underlying neurological causes that create and sustain a variety of eating disorders as well as disorders of those behaviors that contribute to eating disorders. Therefore there remains a need to provide further improvements to treatment methods for eating disorders, and their underlying behaviors, that will further improve the long term success of their efficacy.

BRIEF DESCRIPTION OF THE DRAWINGS

For a more complete understanding of some representative embodiments, reference is now made to the following descriptions taken in conjunction with the accompanying drawings.

DETAILED DESCRIPTION

Figure 1:
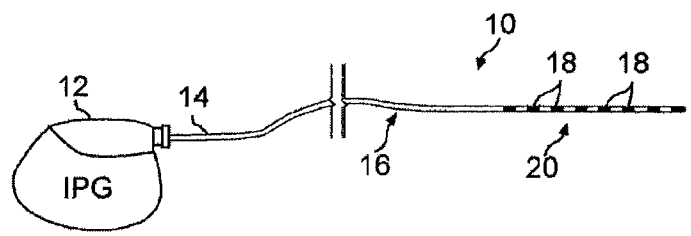
FIGS. 1A and 1B illustrate example electrical stimulation systems.
Figure 1:
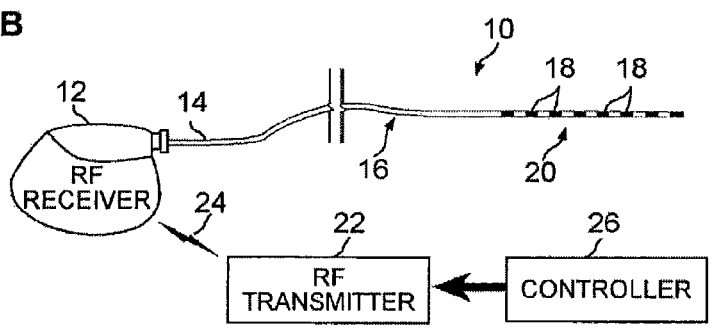

It is readily apparent to one skilled in the art that various embodiments and modifications can be made to the representative embodiments in this application without departing from the scope of the appended claims.

I. DEFINITIONS

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, the term "Brodmann area 25" refers to the defined area of Brodmann area 25 as known by one of skill in the art, as well as the surrounding or adjacent white matter tracts leading to and from Brodmann area 25 and/or white matter tracts that are immediately contiguous with Brodmann area 25.

As used herein, the term "Brodmann area 24" refers to the defined area of Brodmann area 24 as known by one of skill in the art, as well as the surrounding or adjacent white matter tracts leading to and from Brodmann area 24 and/or white matter tracts that are immediately contiguous with Brodmann area 24.

As used herein, the term "Brodmann area 9" refers to the defined area of Brodmann area 9 as known by one of skill in the art, as well as the surrounding or adjacent white matter tracts leading to and from Brodmann area 9 and/or white matter tracts that are immediately contiguous with Brodmann area 9.

As used herein, the term "Brodmann area 10" refers to the defined area of Brodmann area 10 as known by one of skill in the art, as well as the surrounding or adjacent white matter tracts leading to and from Brodmann area 10 and/or white matter tracts that are immediately contiguous with Brodmann area 10.

As used herein the term "depression" refers to a morbid sadness, dejection, or melancholy.

As used herein, the term "in communication" refers to one or more electrical stimulation leads and/or catheters being adjacent, in close proximity, or directly next to, or in direct contact or directly in the predetermined stimulation site. Thus, one of skill in the art understands that the one or more electrical stimulation leads and/or catheters are "in communication" with the predetermined site of the brain if the stimulation results in a modulation of neuronal activity associated with a site. Still further, "in communication" with brain tissue encompasses surrounding or adjacent white matter tracts or fibers leading to and from the brain tissue and/or white matter tracts or fibers that are immediately contiguous with the brain tissue.

As used herein the term "limbic system" encompasses the amygdala, hippocampus, septum, cingulate gyrus, cingulate cortex, hypothalamus, epithalamus, anterior thalamus, mammillary bodies, and formix. The limbic system has connections throughout the brain, more particularly with the primary sensory cortices, including the rhinencephalon for smell, the autonomic nervous system via the hypothalamus, and memory areas. Yet further, the limbic system is involved in mood, emotion and thought.

As used herein the term "mania" or "manic" refers to a disordered mental state of extreme excitement.

As used herein the term "mood" refers to an internal emotional state of a person.

As used herein the term "mood disorder" is typically characterized by pervasive, prolonged, and disabling exaggerations of mood and affect that are associated with behavioral, physiologic, cognitive, neurochemical and psychomotor dysfunctions. The major mood disorders include, but are not limited to major depressive disorder (also known as unipolar disorder), bipolar disorder (also known as manic depressive illness or bipolar depression), dysthymic disorder. Other mood disorders may include, but are not limited to major depressive disorder, psychotic; major depressive disorder, melancholic; major depressive disorder, seasonal pattern; postpartum depression; brief recurrent depression; late luteal phase dysphoric disorder (premenstrual dysphoria); and cyclothymic disorder.

As used herein the term "modulate" refers to the ability to regulate positively or negatively neuronal activity. Thus, the term modulate can be used to refer to an increase, decrease, masking, altering, overriding or restoring neuronal activity. Modulation of neuronal activity affects psychological and/or psychiatric activity of a subject.

As used herein, the term "neuronal" refers to a neuron which is a morphologic and functional unit of the brain, spinal column, and peripheral nerves.

As used herein, the term "pharmaceutical" refers to a chemical or agent that is used as a drug. Thus, the term pharmaceutical and drug are interchangeable.

As used herein, the term "stimulate" or "stimulation" refers to electrical, chemical, and/or magnetic stimulation that modulates the predetermined sites in the brain.

As used herein, the term "subcallosal area" includes the medial gray matter and white matter under the corpus callosum, as well as the white matter tracts that are associated with the subcallosal area. Associated white matter tracts includes the surrounding or adjacent white matter tracts leading to or from a subcallosal area or white matter tracts that are immediately contiguous with the subcallosal area. For the purposes of the present application, the subcallosal area includes the following gray matter and the white matter tracts, as well as the white matter tracts that are associated with or leading to or from the following areas: subgenual cingulate area, subcallosal cingulate area, ventral/medial prefrontal cortex area, ventral/medial white matter, Brodmann area 24, Brodmann area 25, and/or Brodmann area 10.

As used herein, the term "subgenual cingulate area" includes the gray matter and white matter tracts associated with the subgenual cingulate area, the white matter tracts that surround or adjacent to the subgenual cingulate area, or the white matter tracts that lead to or from the subgenual cingulate area. The subgenual cingulate area includes Brodmann area 25 and the subgenual portion of Brodmann area 24.

As used herein, the term "treating" and "treatment" refers to modulating certain areas of the brain so that the subject has an improvement in the disease, for example, beneficial or desired clinical results. For purposes of this application, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. ELECTRICAL STIMULATION DEVICES

FIGS. 1A and 1B illustrate example electrical stimulation systems or devices 10 used to provide deep brain stimulation. Stimulation system 10 generates and applies a stimulus to a target area of the brain, for example, a target area of a subcallosal area, more particularly, a subgenual cingulate area. Still further, the target area can comprise Brodmann area 25 and/or Brodmann area 24. In general terms, stimulation system 10 includes an implantable electrical stimulation source 12 and an implantable electrical stimulation lead 14 for applying the stimulation signal to the target brain tissue. In operation, both of these primary components are implanted in the person's body. Stimulation source 12 is coupled to a connecting portion 16 of electrical stimulation lead 14. Stimulation source 12 controls the electrical signals transmitted to electrodes 18 located on a stimulating portion 20 of electrical stimulation lead 14, located adjacent the target brain tissue, according to suitable signal parameters (i.e., duration, intensity, frequency, etc.). A doctor, the patient, or another user of stimulation source may directly or indirectly input signal parameters for controlling the nature of the electrical stimulation provided.

Another exemplary stimulation system or device includes a microstimulator Bion™, manufactured by Advanced Bionics Corporation) in which the device contains a signal generating portion and at least one electrode in a the same unit or single unit, as defined in U.S. Pat. Nos. 6,051,017; 6,735,475 and 6,735,474, each of which are incorporated herein in its entirety. In further embodiments, a lead assembly is associated with at least one electrode of the microstimulator such that the lead can stimulate the predetermined site not in contact with the microstimulator.

In one embodiment, as shown in FIG. 1A, stimulation source 12 includes an implantable pulse generator (IPG). One of skill in the art is aware that any commercially available implantable pulse generator can be used in the present application, as well as a modified version of any commercially available pulse generator. Thus, one of skill in the art would be able to modify an IPG to achieve the desired results. An exemplary IPG is the BRIO☐ IPG available from St. Jude Medical, Inc. Another example of an IPG is shown in FIG. 1B, which shows stimulation source 12 including an implantable wireless receiver. An example of a wireless receiver may be the Renew☐ System, also available from St. Jude Medical, In. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the signal parameters of electrical signals transmitted through electrical stimulation lead 14 to the stimulation site.

FIGS. 2A through 2D illustrate example electrical stimulation leads 14 that may be used to provide electrical stimulation to an area of the brain, however, one of skill in the art is aware that any suitable electrical lead may be used. As described above, each of the one or more leads 14 incorporated in stimulation system 10 includes one or more electrodes 18 adapted to be positioned near the target brain tissue and used to deliver electrical stimulation energy to the target brain tissue in response to electrical signals received from stimulation source 12. A percutaneous lead 14, such as example leads shown in FIG. 2A-2D, includes one or more circumferential electrodes 18 spaced apart from one another along the length of lead 14. Circumferential electrodes 18 emit electrical stimulation energy generally radially in all directions.

III. IMPLANTATION OF ELECTRICAL STIMULATION DEVICES

While not being bound by the description of a particular procedure, patients who are to have an electrical stimulation lead or electrode implanted into the brain, generally, first have a stereotactic head frame, such as the Leksell, CRW, or Compass, mounted to the patient's skull by fixed screws. However, frameless techniques may also be used. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and the patient's skull, so that either a person or a computer software system can adjust and calculate the correlation between the real world of the patient's head and the virtual space model of the patient's MRI scans. The surgeon is able to target any region within the stereotactic space of the brain with precision (i.e., within 1 mm). Initial anatomical target localization is achieved either directly using the MRI images, or indirectly using interactive anatomical atlas programs that map the atlas image onto the stereotactic image of the brain. As is described in greater detail below, the anatomical targets may be stimulated directly or affected through stimulation in another region of the brain.

Figure 3:
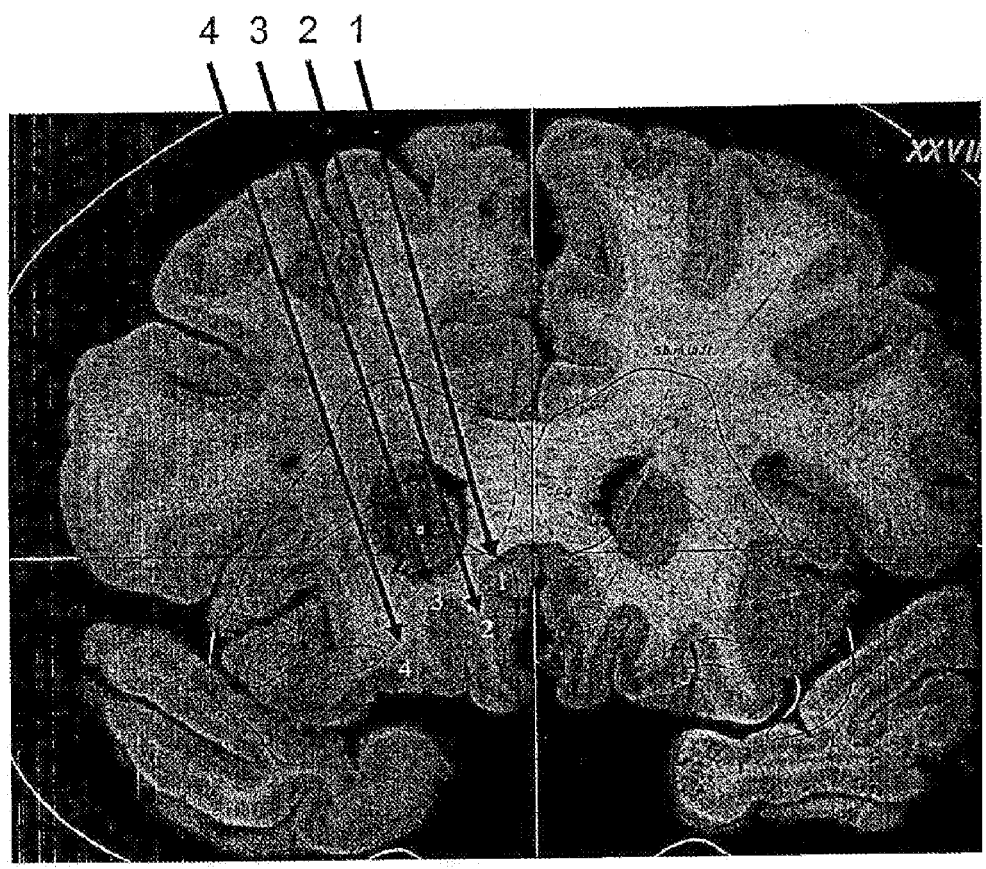
FIG. 3 is a coronal (front vertical) section of a human brain showing arrows directed to target areas.

With reference to FIG. 3, this shows the position of the subcallosal area having coordinates derived from the Schaltenbrand and Wahren Atlas plate 3 coronal section through the brain are 6-7 mm from the midline (range 2-14 mm), 29 mm anterior to the mid-commissural point range (20-40) and 5 mm (range 0-10 mm) below the intra-commissural line. Referring to FIG. 3, arrow 1 points to the subgenual cingulate area, more particularly Brodmann area 25; arrow 2 points to the gyrus rectus area; arrow 3 points to the subcaudate area; and arrow 4 points to the orbitofrontal area.

Figure 5A:
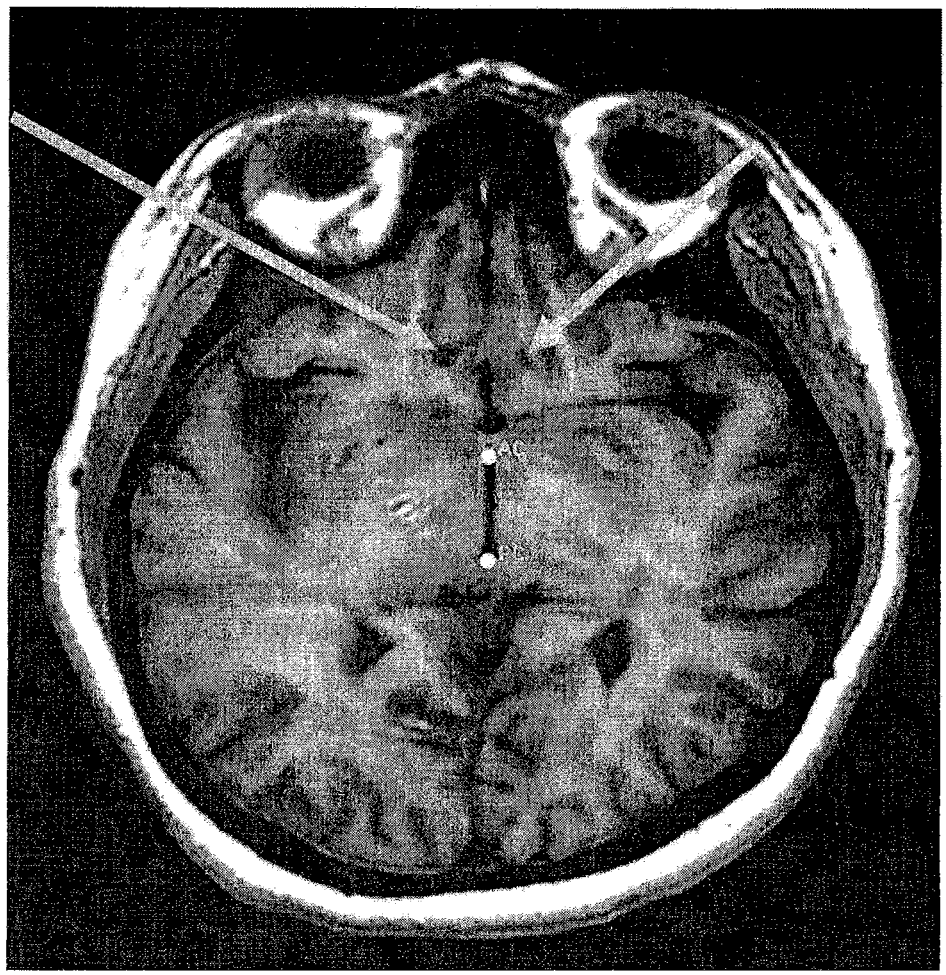
FIGS. 5A-5D show scans through various planes of the brain.
Figure 5B:
Figure 5C:
Figure 5D:
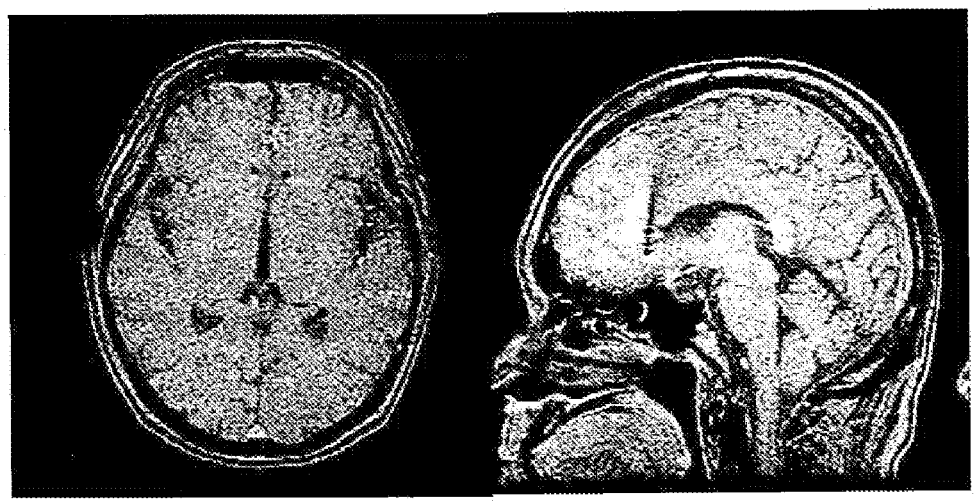
Figure 6:
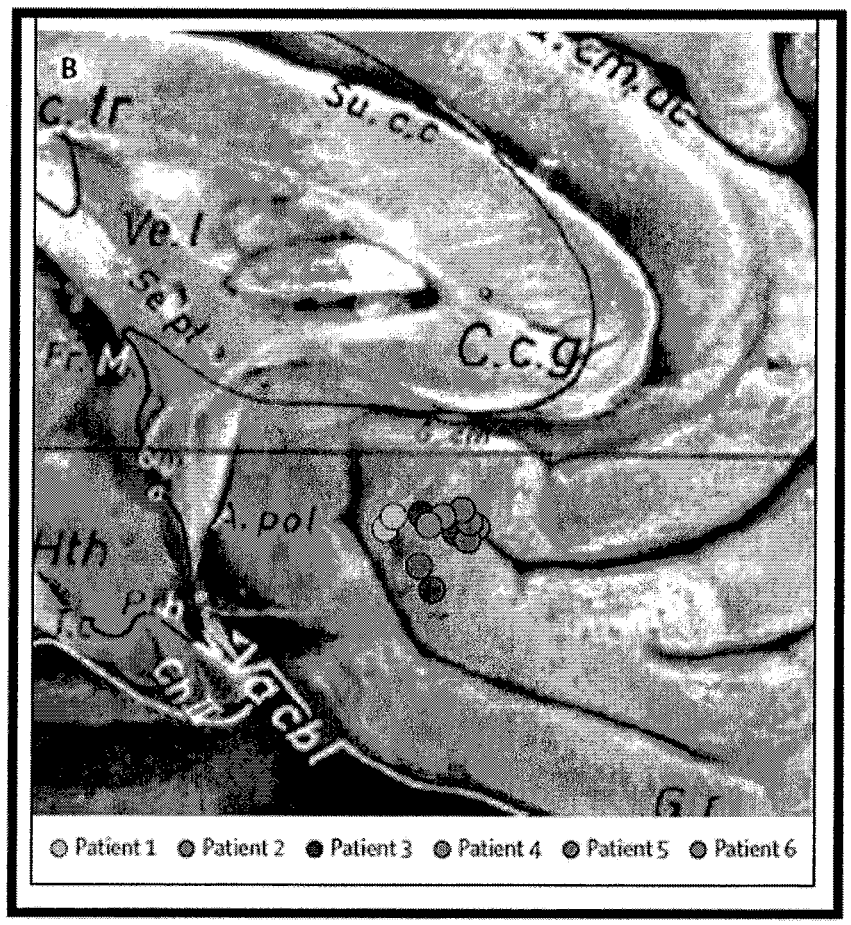
FIG. 6 depicts electrode locations for respective patients that received DBS for treatment of anorexia.

FIG. 5A shows a T1 MRI in the horizontal plane showing the tips (at arrows) on the implanted lead 4 contact electrodes positioned anterior to the anterior commissure (AC), approximately 7 mm from the midline and below the plane of the inter-commissural line, in a patient with depression. FIG. 5B shows an axial T1 MRI in the horizontal plane of a patient with depression implanted with chronic deep brain stimulating electrodes to stimulate subcallosal white matter and adjacent cortex including subgenual cingulate gyrus, particularly Brodmann area 25/Brodmann area 24. FIG. 5C shows a T1 weighted MRI Coronal view of a patient having scans of FIGS. 5A and 5B showing right and left electrodes in the plane of the brain corresponding to the Schaltebrand and Warren atlas section plate 3 shown in FIG. 3. The central dot is the midline. FIG. 5D shows T1 weighted MRI images of a second patient with bilateral electrodes implanted to stimulate subcallosal white matter and adjacent cortex including subgenual cingulate gyrus, particularly Brodmann area 25/Brodmann area 24.

Based upon the coordinates derived or described above, the electrical stimulation lead 14 can be positioned in the brain. Typically, an insertion cannula for electrical stimulation lead 14 is inserted through the burr hole into the brain, but a cannula is not required. For example, a hollow needle may provide the cannula. The cannula and electrical stimulation lead 14 may be inserted together or lead 14 may be inserted through the cannula after the cannula has been inserted.

Once an electrical stimulation lead, such as lead 14, has been positioned in the brain, the lead is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14 is laid substantially flat along the skull. Where appropriate, any burr hole cover seated in the burr hole may be used to secure electrical stimulation lead 14 in position and possibly to help prevent leakage from the burr hole and entry of contaminants into the burr hole.

Once electrical stimulation lead 14 has been inserted and secured, connecting portion 16 of lead 14 extends from the lead insertion site to the implant site at which stimulation source 12 is implanted. The implant site is typically a subcutaneous pocket formed to receive and house stimulation source 12. The implant site is usually positioned a distance away from the insertion site, such as near the chest, below the clavicle or alternatively near the buttocks or another place in the torso area. Once all appropriate components of stimulation system are implanted, these components may be subject to mechanical forces and movement in response to movement of the person's body. A doctor, the patient, or another user of stimulation source may directly or indirectly input signal parameters for controlling the nature of the electrical stimulation provided.

Although example steps are illustrated and described, the present application contemplates two or more steps taking place substantially simultaneously or in a different order. In addition, the present application contemplates using methods with additional steps, fewer steps, or different steps, so long as the steps remain appropriate for implanting an example stimulation system into a person for electrical stimulation of the person's brain.

IV. INFUSION PUMPS

In further embodiments, it may be desirable to use a drug delivery system independent of or in combination with electrical stimulation of the brain. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, without being bound to a specific procedure, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any suitable type of infusion pump can be used to deliver an appropriate therapeutic agent. For example, "active pumping" devices or so-called peristaltic pumps are described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device.

Other pumps that may be used include accumulator-type pumps, for example certain external infusion pumps. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666,845, 6,620,151 which are incorporated by reference in its entirety.

Instances in which chemical and electrical stimulation will be administered to the subject, a catheter having electrical leads may be used, similar to the ones described in U.S. Pat. Nos. 6,176,242; 5,423,877; 5,458,631 and 5,119,832, each of which are incorporated herein by reference in its entirety.

V. TREATMENT OF AN EATING DISORDER

Initially, there is an impetus to treat psychiatric disorders with direct modulation of activity in that portion of the brain causing the pathological behavior. In this regard, there have been a large number of anatomical studies that have helped to identify the neural structures and their precise connections which are implicated in psychiatric activity/disorders. These are the structures that are functioning abnormally and manifesting in psychiatric/behavioral/addiction disorders. Numerous anatomical studies from autopsies, animal studies, and imaging such as computerized tomography (CT) scans, and magnetic resonance imaging (MRI) scans have demonstrated the role of these structures and their connections in psychiatric activity/disorders. In addition to these anatomical studies, a number of physiological techniques and diagnostic tools are used to determine the physiological aberrations underlying these disorders. This includes electrical methods such as electroencephalography (EEG), magnetoencephalography (MEG), as well as metabolic and blood flow studies such as functional magnetic resonance imaging (fMRI), and positron emission tomography (PET). The combination of the anatomical and physiological studies have provided increased insight into the understanding of the structures which are involved in the normal functioning or activity of the brain and the abnormal functioning manifesting in psychiatric, behavioral and addiction disorders.

Accordingly, the present application relates to modulation of neuronal activity to affect psychological or psychiatric activity and/or mental activity related to an eating disorder in a patient. The present application finds particular application in the modulation of neuronal function or processing to affect a functional outcome. The modulation of neuronal function is particularly useful with regard to the prevention, treatment, or amelioration of psychiatric, psychological, conscious state, behavioral, mood, and thought activity (unless otherwise indicated these will be collectively referred to herein as "psychological activity" or "psychiatric activity" or "mental activity") and may include, but not be limited to, normal functions such as alertness, conscious state, drive, fear, anger, anxiety, euphoria, sadness, and the fight or flight response.

One technique that offers the ability to affect neuronal function is the delivery of electrical, chemical, and/or magnetic stimulation for neuromodulation directly to target tissues via an implanted device having a probe. The probe can be a stimulation lead or electrode assembly or drug-delivery catheter, or any combination thereof. The electrode assembly may be one electrode, multiple electrodes, or an array of electrodes in or around the target area. The proximal end of the probe can be coupled to a device, such as an electrical signal source, pharmaceutical delivery pump, or both which, in turn, is operated to stimulate the predetermined treatment site. In certain embodiments, the probe can be incorporated into the device such that the probe and the signal generating device are a single unit.

Certain embodiments involve a method of treating an eating disorder comprising the steps of: surgically implanting an electrical stimulation lead having a proximal end and a stimulation portion, wherein after implantation the stimulation portion is in communication with a predetermined site; coupling the proximal end of the lead to a signal generator; and generating an electrical signal with the signal generator to modulate the predetermined site thereby treating the eating disorder.

In further embodiments, neuromodulation of the predetermined site can be achieved using magnetic stimulation. One such system that can be employed and that is well known in the art is described in U.S. Pat. No. 6,425,852, which is incorporated herein by reference in its entirety.

The therapeutic system or deep brain stimulation system is surgically implanted as described in the above sections. One of skill in the art is cognizant that a variety of electrodes or electrical stimulation leads may be utilized. It is desirable to use an electrode or lead that contacts or conforms to the target site for optimal delivery of electrical stimulation. One such example, is a single multi contact electrode with eight contacts separated by 2½ mm each contract would have a span of approximately 2 mm. Another example is an electrode with two 1 cm contacts with a 2 mm intervening gap. Yet further, another example of an electrode that can be used is a 2 or 3 branched electrode/catheter to cover the predetermined site or target site. Each one of these three pronged catheters/electrodes have four contacts 1-2 mm contacts with a center to center separation of 2 of 2.5 mm and a span of 1.5 mm. Similar designs with catheters to infuse drugs with single outlet pore at the extremities of these types of catheters or along their shaft may also be designed and used.

The predetermined site or target area is a subcallosal area, more preferably, the subgenual cingulate area, and more preferably Brodmann area 25/Brodmann area 24. Stimulation of a subcallosal area (i.e., subgenual cingulate area or Brodmann area 25/Brodmann area 24) and/or the surrounding or adjacent white matter tracts leading to or from the subcallosal area or white matter tracts that are immediately contiguous with the subcallosal area results in changes that alleviate or improve the mood and/or anxiety disorder of the subject. It is contemplated that modulating a subcallosal area, more particularly a subgenual cingulate area, can result in increasing, decreasing, masking, altering, overriding or restoring neuronal activity resulting in treatment of the mood and/or anxiety disorder. Yet further stimulation of a subgenual cingulate area, more particularly Brodmann area 25, results in modulation of neuronal activity of other areas of the brain, for example, Brodmann area 9, Brodmann area 10, Brodmann area 24, the hypothalamus, and the brain stem.

Using the therapeutic stimulation system, the predetermined site or target area is stimulated in an effective amount or effective treatment regimen to decrease, reduce, modulate or abrogate the eating disorder. Thus, a subject is administered a therapeutically effective stimulation so that the subject has an improvement in the parameters relating to the eating disorder including subjective measures such as, for example, neurological examinations and neuropsychological tests (i.e., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as antidepressants, or other alterations in cerebral blood flow or metabolism and/or neurochemistry. The improvement is any observable or measurable improvement. Thus, one of skill in the art realizes that a treatment may improve the patient condition, but may not be a complete cure of the disease.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

According to one embodiment, the target site is stimulated using stimulation parameters such as, pulse width of about 1 to about 500 microseconds, more preferable, about 1 to about 90 microseconds; frequency of about 1 to about 300 Hz, more preferably, about 100 to about 185 Hz; and voltage of about 0.5 to about 10 volts, more preferably about 1 to about 10 volts. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

It is envisioned that stimulation of a subcallosal area and/or the adjacent white matter modulates other targets in the limbic-cortical circuit or pathway thereby improving any dysfunctional limbic-cortical circuits resulting in an improvement or alleviation or providing remission of depression and/or anxiety in the treated subjects. Other such improvements can be sensations of calm, tranquility, peacefulness, increased energy and alertness, improved mood, improvement in attention and thinking, improvement in motor speed, improvement in mental speed and in spontaneity of speech, improved sleep, improved appetite, improved limbic behavior, increased motivation, decreases in anxiety, decreases in repetitive behavior, impulses, obsessions, etc.

For purposes of this application, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether objective or subjective.

Figure 4:
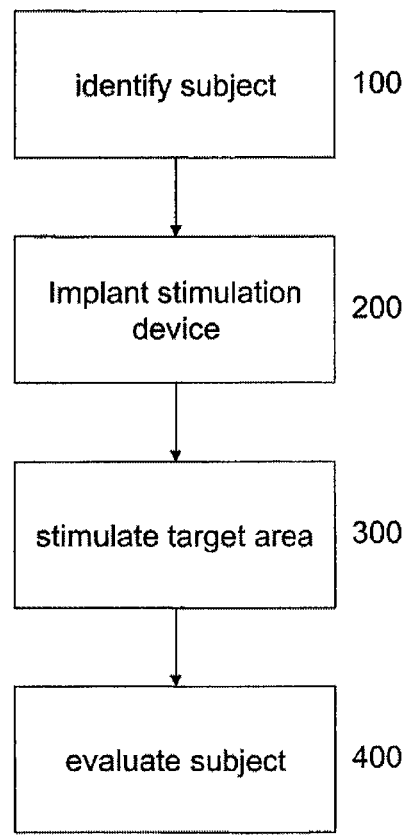
FIG. 4 is a flowchart describing the general procedure.

FIG. 4 summarizes the general procedure according to one representative embodiment. Any of the above described methods can be used to identify a subject or diagnose a subject that suffers from an eating disorder (100). Once the subject is identified, a stimulation device is implanted (200) into the subject such that the subcallosal area of the subject's brain is stimulated (300). After the target area has been stimulated (i.e., electrical, chemical or magnetic stimulation), the subject is evaluated to determine the change in the eating disorder. One of skill in the art realizes that the present application is not bound by the described methods or devices and that any method or device that would result in neuromodulation of the subcallosal area could be used.

VI. COMBINATION TREATMENT

In order to increase the effectiveness of the electrical stimulation method, it may be desirable to combine electrical stimulation with chemical stimulation to treat the eating disorder.

In one preferred alternative, an implantable signal generator and electrical stimulating lead and an implantable pump and catheter(s) are used to deliver electrical stimulation and/or one or more stimulating drugs to the above mentioned areas as a treatment for eating disorders.

Herein, stimulating drugs comprise medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

VII. EXAMPLES

Anorexia Nervosa (AN) is characterized by a chronic course that is refractory to treatment in many patients and has one of the highest mortality rates of any psychiatric disorder.

A phase I prospective trial of subcallosal cingulate cortex (SCC) Deep Brain Stimulation (DBS) in six (6) patients with chronic, severe and treatment-refractory was completed. Eligible patients underwent medical optimization preoperatively and had baseline psychometric and neuroimaging investigations followed by implantation of electrodes and a pulse generator for continuous delivery of electrical stimulation. The trial is discussed in Subcallosal cingulate deep brain stimulation for treatment-refractory anorexia nervosa: a phase 1 pilot trial, the Lancet, Volume 381, Issue 9875, 20-26 Apr. 2013, Pages 1361-1370, which is incorporated herein by reference.

After stimulation for 9-months, 3/6 patients (50%) had achieved and maintained a body-mass index (BMI) significantly greater than historic baseline, constituting an important change in the natural history of their condition. DBS was associated with significant improvements in mood, anxiety, affective regulation, and AN-related obsessions and compulsions in 4/6 patients (67%) at 6-months post surgery. These clinical benefits were accompanied by changes in cerebral glucose metabolism consistent with a reversal of the abnormalities seen in the anterior cingulate, insula and parietal lobe found in AN.

SCC DBS appears to be safe in this sample of patients with chronic and treatment-refractory AN, and is associated in some patients, with sustained improvements in BMI, mood, and anxiety.

Chronic stimulation resulted in network-wide metabolic changes in brain structures involved in depressed mood, body image, and food-related behavior.

Anorexia Nervosa (AN) has a mortality rate of 6-11% and is among the most challenging psychiatric conditions to treat. With an estimated prevalence of 0.3-0.9%, AN is typically diagnosed in female young adults between ages 15-19, and is among the most common psychiatric condition in this age group. The condition is characterized by a refusal to maintain a healthy body weight, a persistent fear of gaining weight, a relentless drive for thinness, as well as preoccupations with body-image and self-perception. Psychological factors, such as perfectionism, anxiety, affective dysregulation and reward processing abnormalities, have been proposed as prominent perpetuating, as well as etiological, factors in AN. Current treatment strategies are aimed at the acute and chronic stages of the illness. Acute care entails medical stabilization in severely underweight and metabolically unstable patients. Rapid fluctuations in weight, severe restriction, and bingeing and purging behavior, are associated with significant medical complications, leading to cardiac dysrhythmias, musculoskeletal and neurologic symptoms.

Intensive treatment, in an inpatient or outpatient/day hospital setting, focuses on behavioural change as well as addressing underlying and disease maintaining factors. AN is most commonly a chronic illness, with a waxing and waning course. Up to 20% of patients derive no sustained benefit from currently available treatment programs and are at risk for premature death. Despite decades of investigation, the factors associated with mortality and progression to chronic illness are poorly understood.

The circuitry and biology of AN are areas of active investigation, with most disease models focusing on structures underlying pathologic mood, anxiety, reward and body perception/interoception. Much of this work is driven by neuroimaging, which has demonstrated both structural and functional differences between AN patients and healthy controls. The most consistent features are parietal area hypometabolism, as well as limbic circuit dysfunction, including increased activity and decreased 5HT2A binding in the subcallosal area, a region that is known to be important in mood regulation, underscoring the importance of perceptual and mood disturbances in the condition.

Deep Brain Stimulation (DBS) is a neurosurgical procedure performed for over 25 years to modulate the activity of dysfunctional brain circuits. It has been shown to be effective and safe in patients with Parkinson's disease and essential tremor and its use has now been extended to other circuit-based neuropsychiatric disorders, such as major depression, obsessive-compulsive disorder, Tourette's syndrome, and Alzheimer's disease.

DBS is a non-lesional and adjustable procedure that exerts its effect both locally and remotely, across mono- and poly-synaptically linked networks.

The subcallosal cingulate (SCC) was selected as a target for DBS in AN for the following three reasons: i) Imaging studies show similar patterns of activity in the SCC region, and its afferent and efferent projections, in AN as in depression patients ii) AN, mood and anxiety disorders are frequently co-morbid, with similar anatomic structures and circuits implicated. Several studies have also shown that treating weight alone in AN patients leads to faster relapse, while treating comorbid mood and anxiety symptoms is associated with improved outcomes, and more complete and long-lasting recovery suggesting these are important symptoms to target; and, iii) SCC DBS improves symptoms in treatment-refractory depression patients and reverses cerebral metabolic abnormalities in dysfunctional limbic circuits. With the evidence of shared symptoms and circuitry, it was postulated by the current inventor that SCC DBS could also be helpful in AN.

To examine this possibility, a pilot, phase I trial of SCC DBS in 6 patients with chronic, treatment-refractory AN was designed.

The trial was registered with clinicaltrials.gov and approved by the Research Ethics Board (REB). Patients were identified through the Eating Disorders Program at Toronto General Hospital as well as through community referrals to the study. The intent was to offer this procedure only to patients who might be expected to continue on with a chronic illness and/or die a premature death because of the severity of their condition. There are no established consensus operational criteria in the AN field to identify treatment refractory patients. Accordingly, a set of criteria was developed, which is believed to represent a best effort to select such patients as subjects for the study. The inclusion criteria included: Female or male patients between age 20-60; Diagnosis of Anorexia Nervosa, restricting or binge-purging subtype as defined by the Diagnostic and Statistical Manual (DSM-IV-TR); Chronicity and/or treatment resistance demonstrated by some or all of: a pattern of three years duration of relentless unresponsiveness to repeated; voluntary hospitalizations, characterized by failure to complete treatment or immediate weight relapse following treatment; a pattern of increasing medical instability accompanied by refusal to participate; in/lack of responsiveness to intensive expert treatment and increasing medical acuity, lasting at least two years and involving at least two episodes of involuntary feeding; a pattern of chronic stable AN lasting at least 10 years; able to provide informed consent; able to comply with all testing, follow-ups and study appointments and protocols. The exclusion criteria included: any past or current evidence of psychosis; active neurologic disease such as epilepsy; alcohol or substance dependence or abuse in the last 6 months, excluding caffeine and nicotine; any contraindication to MRI or PET scanning; likely to relocate or move during the study's one year duration; BMI less than 13; presence of cardiac arrhythmias, or other cardiac, respiratory, renal or endocrine conditions as a result of AN or not, that will result in significant risk from a surgical procedure; and pregnancy.

Following initial screening for eligibility and team discussion, patients were referred to an independent, non-study affiliated psychiatrist for independent evaluation of the diagnosis, treatment refractoriness, study eligibility and review of capacity to consent.

Once enrolled, patients underwent baseline psychometric assessments using depression, anxiety and eating disorder inventories (Hamilton Depression Rating Scale [HDRS], Beck Depression Inventory [BDI], Beck Anxiety Inventory [BAI], Yale-Brown Obsessive Compulsive Scale [YBOCS], Yale-Brown-Cornell Eating Disorder Scale in Women [YB-CEDS], Quality of Life Scale). Patients also underwent neuroimaging with magnetic resonance imaging (MRI) and Fluorodeoxyglucose positron emission tomography (18F-

FDG-PET), as well as an anaesthesia consultation for assessment of fitness for surgery.

On the morning of surgery, a stereotactic frame was applied to patients prior to an MRI that was then used to select the target. The anatomic target was a white matter bundle immediately below the genu of the corpus callosum as has been previously used for patients with depression. The procedure was performed with the patients fully awake using local anaesthesia.

Bilateral burr holes were drilled, and electrodes inserted under fluoroscopic guidance. Each of the electrode contacts was stimulated to look for spontaneous reports of mood or anxiety changes or adverse effects. Several patients reported acute responses to blinded stimulation, described in further detail in the supplementary material. An intraoperative AN Rating Scale designed by the research team to probe changes to AN cardinal symptoms with stimulation was also administered at individual contacts, with frequency and amplitude kept constant. Responses were noted and videotaped for subsequent analysis. Once testing was complete the electrodes were internalized and connected to a subcutaneously implanted pulse generator placed below the right clavicle, with the patient under general anaesthesia. Patients underwent a structural MRI for electrode position confirmation on the first post-operative day and discharged from hospital with the stimulator off.

Patients were seen ten days following discharge for device activation. Initial stimulating contacts were those that either: i) elicited the most significant acute mood and anxiolytic responses in the operating room; and/or, ii) were the ones closest to the anatomic SCC on postoperative MRI. All patients were started at an amplitude of 3.5V, pulse width 90 microseconds, and frequency 130 Hz. Stimulation parameter changes were made in conjunction with patient and physician feedback. Frequency and pulse width remained unchanged for the duration of the study, with amplitudes ranging from 5 to 7V in all patients. No medication changes were made in the first three months following DBS surgery. Psychometrics were repeated at 1,3- and 6-months following device activation. FDG-PET and structural MRI were repeated at 6 months post-activation.

As a pilot study, primary outcome measures were adverse events surrounding surgery as well as those related to acute and chronic stimulation. Adverse events were monitored for at every study visit. Secondary outcomes related to weight (BMI), mood and anxiety measures (BDI, BAI, HAMD-17, YBOCS, YBC-EDS), as well as AN-related hospital admissions.

PET scans with the radiotracer [18F]-2-deoxy-2-fluoro-D-glucose to measure regional cerebral glucose metabolism were acquired preoperatively and after 6 months of continuous DBS.

Six (6) patients were enrolled in the pilot trial. All patients were female with an average age at surgery of 38.3 (range 24-57). All patients met DSM-IVTR criteria for Anorexia Nervosa, with average age at diagnosis of 20, and mean duration of illness of 18.3 years prior to receiving DBS. Five patients had a history of recurrent acute hospital admissions for medical stabilizations with four patients having had ten or more hospitalizations. Following study enrollment, all patients required some form of medical optimization prior to surgery, including either inpatient treatment or close outpatient follow-up to ensure they continued to meet study entrance criteria. All patients except one, the oldest, had comorbid psychiatric conditions, with major depressive disorder (MDD) and obsessive-compulsive disorder (OCD) the most common. All patients were currently, or had previously, suffered multiple medical complications related directly to their AN.

There is no agreed upon methodology to make estimates of average, or typical BMI in patients with chronic AN. Weight fluctuations related to hospitalizations, voluntary or emergency, are common. To obtain an adequate estimation of baseline BMI, medical records were reviewed for the 5-7 years preceding study enrolment, conducted patient interviews and examined patients' weight diaries. This revealed a mean baseline BMI of 13.7 for enrolled patients. At the initial study screening visit, conducted within 6-8 weeks of surgery, most patients (1, 2, 3, 4, and 5) had recently been attending inpatient treatment resulting in some weight gain. It is typical for this patient group to be in and out of hospital depending on their physical condition, with fluctuations in weight as a consequence. As a result, mean pre-operative BMI was 16.1, a value significantly higher than the typical baseline BMI for these patients.

At two months following surgery, all patients had lost weight from their pre-operative BMI. This drop in weight may represent a regression towards the baseline as would be expected by the natural history of the illness, and given the fact that the pre-operative BMI was likely an artifact of recent inpatient admission. At 3-months, however, this pattern began to reverse, with all patients except one, gaining weight or stabilized. Two patients (1 and 5) at 6-months were at a BMI greater than that at surgery, while at 9-months, three patients (1, 2 and 5) were maintaining BMI's that were significantly higher than baseline. For all three patients, this was the longest period of a sustained BMI increase since the onset of their illness (mean 17 years). The remaining three patients were at a BMI at 9-months within 0.3 points of their historic baseline, indicating that DBS had no apparent impact, positive or negative, on these patients' weight fluctuations or baseline.

Both physician and patient mood ratings showed changes after the initiation of stimulation. Mean pre-operative HAMD scores for all 6 patients was 1.·8, decreasing to 12.5 at 3-months and 10.7 at 6-months. At baseline, the majority of patients (1, 2, 4, and 5) had HAMD scores indicating a severe depression (HAMD>20). Three of these four patients (1, 2, and 5) were classified as treatment responders at 6-months (defined as >50% reduction in HAMD score), with one patient (5) achieving remission (HAMD<7). BDI scores for enrolled patients decreased from a pre-operative mean of 38.8 to a mean of 20.2 at 6-months. Mean YBOCS score at baseline was 25, decreasing to 15.8 at 3-months and 13.2 at 6-months.

Five patients met clinical criteria for OCD at baseline (1, 2, 3, 5, and 6), and three of these were clinical responders at 6-months (2, 5, and 6), defined by a reduction in YBOCS scores of greater than 35%. Subjective anxiety measures were also significantly reduced at 6-months, with BAI values dropping from a pre-surgical mean of 31.2, to 21.7 at final follow-up (FIG. 3). Eating disorder specific attitudes were assessed pre- and post-operatively. Scores related to food and weight pre-occupations as well as eating disorder rituals both decreased over the course of the study (pre-occupations pre-operative mean 23.7 vs. 6-month mean 17.7; rituals pre-operative mean 29.3 vs. 6-month mean 19).

Figure 2:
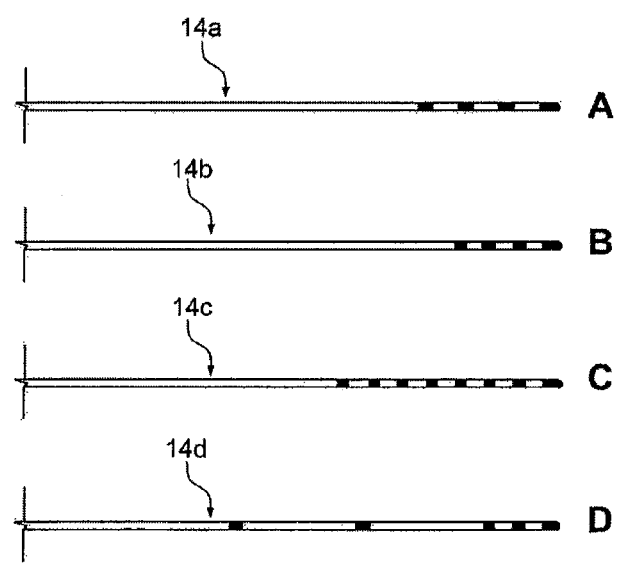
FIGS. 2A-2D illustrate example electrical stimulation leads that may be used to stimulate a patient according to some representative embodiments.

Three patients (1, 2 and 5) experienced a significant deviation in the natural history of their illness in the months following DBS surgery, as defined by changes in all of weight, mood, anxiety and treatment engagement (See supplementary FIG. 2, for example). Two patients who had the greatest improvements in BMI (1 and 5), were voluntarily admitted at 3-months post-op to a specialized inpatient eating disorders program, and completed these for the first time since their initial diagnosis. The remaining patients were managed with routine outpatient care with their AN psychiatrist and/or psychologist.

Four patients (1, 2, 3 and 5) had sustained improvements in affective regulation, subjective mood, urges to binge and purge and significant improvements in interpersonal and familial dynamics. Patients 3 and 5 also had significant improvements in urges to exercise, reducing these dramatically. Patients 2 and 5, who had pre-operative diagnoses of post-traumatic stress disorder (PTSD) secondary to remote traumatic events, reported significant reductions in activation and anxiety related to thinking about their past experiences. For the two remaining patients, patient 4 continued to lose weight, requiring an emergency inpatient admission, and patient 6 remained at a stable weight, but subjectively felt at 6-months that her attitudes towards food and eating were beginning to loosen. This was not reflected in her psychometrics. At 9-months follow-up, all enrolled patients were being treated on an outpatient basis The voxelwise analyses of the SUV data revealed significant changes in cerebral glucose metabolism after six months of DBS. Metabolism was decreased in anterior cortical regions including the right anterior cingulate gyrus [BA24,25], medial frontal gyrus; [left BA 6; right BA 9], and bilateral insula, the left caudate and claustrum and the left cerebellum (culmen, vermis and declive). Metabolism was increased in posterior cortical regions including the right middle and inferior temporal gyrus [BA 20,21], left postcentral gyrus [BA1], right precuneus [BA 7], right supramarginal gyrus [BA 40], right inferior parietal lobule [BA 40] and left cuneus [BA 19].

Surgery was in general well tolerated, but was associated with a number of adverse effects. The average length of hospital-stay post-surgery was 1.3 days, with most patients (4/6) discharged on the first post-operative day. Serious adverse events (SAE) were considered either study or non-study related. There was one study-related SAE, a seizure following DBS programming in a patient who was approximately two weeks post-surgery, and who was experiencing a significant metabolic derangement. The DBS device was turned off, and reactivated one week later. The patient had no history of seizures, and experienced no seizure recurrence in follow-up. There were several non-study related SAEs attributed to the underlying condition, and these included metabolic aberrations and cardiac dysrhythmias. Intraoperatively, one patient experienced a self-limited panic attack during drilling of the skull, and one patient had an air embolus, that resolved with time and re-positioning of the operating table.

DBS in this group of six patients with chronic and treatment-refractory AN was relatively safe, and associated in some patients with significant effects on BMI, mood, anxiety, and brain metabolism. Clinically, 3/6 (50%) patients experienced a change in the natural history of their condition, achieving a sustained BMI increase over a period of months, for the first time in the course of their illness. The clinical and imaging findings are particularly striking given the chronicity, severity and life-threatening nature of the illness in these patients, who combined for a history of close to 50 hospitalizations.

Assessing weight or BMI is an obvious target in a study of this nature. However, the natural history of chronic AN, involves many changes in weight over time, related to emergency medical admissions, voluntary hospitalizations, and frequent episodes of precipitous weight loss. As a result, identifying a 'baseline BMI' as well defining 'weight change' is complex in this patient group. Given the lack of an established mechanism to make this ascertainment, the most comprehensive assessment possible was completed and all available data was collected.

While weight cannot be ignored, for this group of AN patients attempts to determine whether the overall course of the illness is changing may be a more realistic approach to assessing the efficacy of DBS. For example, patients with significant improvements in their affective regulation may have reductions in impulsive behaviors, and improved relationships with others that allow a better response to standard treatments that are heavily weighted towards psychotherapy. Given the high risk of death in the patient population being studied, and their well-established failure to respond to standard treatments, a shift towards being able to make use of such treatments, or an apparent switch to a more stable form of the illness would represent a significant step forward in this particular patient group. Some of the results support this view.

Following surgery all of the patients lost weight at two months, consistent with the natural history of their condition. Most patients began to gain weight or stabilize at two to three months after surgery. The initial weight loss argues against a primary effect of DBS on hunger, appetite or metabolic rate. It also suggests that there is little in the way of a placebo-related benefit to the surgery. Instead, the pattern observed could reflect the impact of mood and anxiety control on AN-related thoughts and behaviors, and hence BMI. Previous work with DBS in such conditions as dystonia and mood and anxiety disorders has shown that the benefits to stimulation are delayed and progressive, and follow a pattern of a latency of 2-3 months. This is similar to the inflection point in mean BMI at two months seen here in AN patients, which tracked with improvement in mood, reflected by reductions in HAMD and BDI scores at 3 months.

The presence of untreated mood and anxiety symptoms portends a worse prognosis and higher rates of relapse in AN. The significant reductions in HAMD scores at 6-months in the patient group are in line with previously reported effects of limbic system DBS on depression, where response rates are typically 50-60%. The additional observed influence on anxiety, reflected in significant YBOCS and BAI score reductions, suggests a broader influence of SCC activity on affective regulation. In most patients, there was a persistent pattern of diminished urge intensity and impulsive decision-making, which often translated into improved interpersonal dynamics. For the two patients who chose to re-enter intensive voluntary treatment, improved affective regulation was a key factor in allowing them to work more effectively than in previous admissions with the treating program team. A third patient was able to enter treatment for an important area of comorbidity for the first time, and complete it successfully. This was accompanied by an improvement in her eating and an increase in her weight.

While the mechanism explaining the improvements are yet to be known the tandem mood and anxiety effects of SCC DBS suggests that the clinical effect observed may not be mediated by the treatment of a depression per se, but rather by restoring equilibrium to a previously dysregulated state. In this way, DBS that is associated with improved mood, anxiety and affective regulation may interfere with important illness-maintaining factors, and could represent a 'foot-in-the-door' in highly refractory cases. Notably, the observation of improvements in mood and anxiety in patients who were still underweight is especially striking, given the well-known lack of response of underweight patients to conventional pharmacotherapies or psychotherapies.

The imaging results of the study demonstrate that SCC DBS has network-wide effects, and influenced structures directly implicated in AN, including the anterior cingulate, insula and parietal lobe.

The results show that DBS of the SCC area in AN patients produces similar decreased SCC and medial frontal and increased parietal activity as are seen with stimulation of this area in patients with treatment-resistant major depression. This suggests that independent of the diagnosis, stimulating this same target can lead to relatively stereotypic cerebral metabolic changes. Decreased SCC and insula and increased parietal activity have also been linked to clinical improvements in depressed mood, following pharmacologic, psychotherapeutic and stimulation-based treatments. Consistent with these findings, similar patterns of changes were observed in glucose utilization in the same regions in the patients, together with significant improvements in depression ratings at 6-months post-DBS. Such findings provide additional evidence for the influence of SCC on downstream limbic structures, as well as for its putative role in the regulation of negative affect.

Metabolic activity in the insula was reduced bilaterally in the patients following 6-months of DBS. The insula figures prominently in current models of AN given its role in fear/anxiety circuitry, taste sensation, and monitoring of one's internal environment, all known to be dysfunctional in AN patients. Although the clinical correlates of insular modulation are unclear, a hypothesized consequence may be to offset over-vigilance to internal milieu. The patients in the study who saw significant improvements in psychometric scores, also reported subjective reductions in fear and disgust surrounding food stimuli, as well as diminished salience of, and attention to, body-shape and AN-maintaining thoughts and behaviours.

Body and weight distortions are defining features of AN and have been linked to parietal lobe dysfunction. Several studies have shown that parietal glucose hypometabolism and hypoperfusion are consistent features of AN, when compared to healthy, age-matched controls. The results show that chronic SCC DBS leads to significant increases in glucose metabolism in the parietal lobe, indicating that remote, AN-relevant structures may be modulated with stimulation.

There are currently no published studies of DBS in a sample of chronic, treatment refractory AN patients. For the trial, patients less than age 20 or with a BMI below 13 were not selected. Selected patients were further required to have a history of long-standing, treatment-refractory AN.

As a phase I pilot trial, it was primarily interested in establishing the safety of DBS in severely ill AN patients. All of the patients had long-standing, life-threatening AN. Several of them had previous admissions to the intensive care unit, with four patients requiring surgical feeding in the past. At 9-months there were no deaths, strokes, infections or serious device-related complications. One unanticipated adverse event included a seizure following device programming, which occurred in the context of a severe metabolic derangement.

Other serious adverse events were related to the underlying illness and were treated promptly and appropriately. Although the experience is limited to six patients, the complication profile of DBS in this population can thus far be presumed to be low.

SCC DBS in a sample of patients with chronic, treatment-refractory AN can safely influence the natural history of the illness, leading in some patients to improved clinical outcomes and congruent cerebral metabolic changes.

In one embodiment, a method of treating an eating disorder in a patient, comprises: diagnosing the eating disorder in the patient; and electrically stimulating a subgenual cingulate cortex site or a ventral medial prefrontal cortex site in the patient using electrodes of an implanted stimulation lead.

The eating disorder may be co-morbid with anxiety and depression. The method may comprise identifying neuronal activity abnormalities in neuronal tissue at one or more selected sites that correlate to anxiety and depression in the patient and any of the neuronal sites referred to herein. The one or more selected sites may include limbic circuit sites. The one or more sites may include a subgenual cingulate cortex site or a ventral medial prefrontal cortex site. An identification of neuronal activity associated with anxiety and/or depression may be applied as part of the treatment protocol as a condition to treating the eating disorder with electrical stimulation. Also, any one or more of the patient criteria selection discussed herein may be applied as a condition of the treatment protocol for determining whether electrical stimulation is appropriate for a given patient.

In some embodiments, the target site for electrical stimulation is either Broadman area 25 or the ventral medial prefrontal cortex. The VMPFC is located in the lower area in the frontal lobe. It is bounded by the cortical regions in the vertical axis which lie from the inferior border of the rostrum of the corpus callosum to the orbital surface of the skull, in the anterior, posterior axis from most posterior most portion of the rostrum of the corpus callosum or the anterior commissure to the frontal surface of the skull, in the medial lateral axis from the midline to 4 cm lateral to the midline. Either the grey matter and/or the white matter tracts leading into or out of these regions can be used as a target site for electrical stimulation. It is likely that the stimulation or drug delivery to multiple points in this region would yield the best results.

Either the depth of the brain or its surface could be targeted with DBS electrodes or chronically implanted cortical surface electrodes connected to an implanted pulse generator similar to the Libra™ or Brio™ pulse generators made by St Jude Medical, Inc. or the Activa™ pulse generator made by Medtronic Inc. The stimulation could be on continuously, in a patient or caregiver activated mode, cycled to daily or monthly rhythms and variations and/or used in a closed loop mode using a physiological, chemical or electrical input signal from the brain. Choosing the correct stimulation parameters is relevant to success of the therapy. The parameters may be the specific parameters discussed herein. Also, the parameters discussed herein may be employed as a starting point for trial stimulation and a patient's specific parameters may be further refined using physiologic feedback, for example, the patients acute response of decreased anxiety and improved mood with stimulation, and decreased adversity to food or looking like a normal woman. Stimulator adjustments could also be made to produce a physiologic signature, fMRI or PET such as seen in the PET figure provided herein.

Although some embodiments and advantages have been described in detail, it should be understood that various changes, substitutions and alterations can be made herein without departing from the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

I claim:

1. A method of treating an eating disorder comprising the steps of:
    surgically implanting an implantable pulse generator and a stimulation lead in a patient with the eating disorder such that multiple electrodes of the stimulation lead are disposed in a subgenual cingulate area below a genu of the corpus callosum of the brain of the patient, wherein the surgically implanting comprises:
        (i) intraoperatively providing acute stimulation to the multiple electrodes of the stimulation lead;
        (ii) intraoperatively evaluating a respective patient response to stimulation on each of the multiple electrodes by assessing a multifactorial patient anxiety scale including measurements of anxiety or depression related to one or more eating disorder behaviors; and
        (iii) programming the implantable pulse generator to provide stimulation to the patient using an electrode selected according to the evaluating; and
    electrically stimulating the subgenual cingulate area by operating the programmed implantable pulse generator, wherein said patient with an eating disorder, (i) exhibits co-morbid moderate or severe depression, (ii) exhibits co-morbid moderate to severe Obsessive Compulsive Disorder, and (iii) exhibits purging behavior or restriction behavior.

2. The method of claim 1, wherein the electrically stimulating results in modulation of neuronal activity in Brodmann area 25 or Brodmann area 24.

3. The method of claim 1, wherein the electrically stimulating results in modulation of neuronal activity in Brodmann area 10 or Brodmann area 9.

4. The method of claim 1 wherein the eating disorder is anorexia nervosa.

5. The method of claim 1 further comprising:
    performing medical imaging to determine metabolic changes in respective areas in the brain of the patient resulting from the electrically stimulating.

6. The method of claim 1 wherein the electrically stimulating applies electrical pulses at a frequency of 130 Hz.

7. The method of claim 1 wherein the electrical stimulating applies electrical pulses with a pulse width of 90 microseconds.

* * * * *